US005571944A

United States Patent [19]
Pfeifer et al.

[11] Patent Number: 5,571,944
[45] Date of Patent: Nov. 5, 1996

[54] ACOUSTIC WAVE (AW) BASED MOISTURE SENSOR FOR USE WITH CORROSIVE GASES

[75] Inventors: Kent B. Pfeifer, Los Lunas; Gregory C. Frye, Cedar Crest; Thomas W. Schneider, Albuquerque, all of N.M.

[73] Assignee: Sandia Corporation, Albuquerque, N.M.

[21] Appl. No.: 359,510

[22] Filed: Dec. 20, 1994

[51] Int. Cl.$^6$ .......................... G01N 29/02; H01L 41/04; H01L 41/18
[52] U.S. Cl. ...................... 73/24.04; 73/24.06; 73/31.05; 310/313 R
[58] Field of Search ............................... 73/23.20, 24.01, 73/24.04, 24.06, 31.05, 31.06; 310/313 R

[56] References Cited

U.S. PATENT DOCUMENTS

| | | | |
|---|---|---|---|
| 4,055,072 | 10/1977 | Fletcher | 73/23 |
| 4,312,228 | 1/1982 | Wohltjen | 73/597 |
| 4,361,026 | 11/1982 | Muller et al. | 73/23 |
| 4,895,017 | 1/1990 | Pyke et al. | 73/24.06 |
| 4,947,677 | 8/1990 | Frye et al. | 73/38 |
| 5,012,668 | 5/1991 | Haworth | 73/24.06 |
| 5,076,094 | 12/1991 | Frye et al. | 73/19.03 |
| 5,117,146 | 5/1992 | Martin et al. | 310/313 R |
| 5,187,980 | 2/1993 | Blair et al. | 73/599 |
| 5,235,235 | 8/1993 | Martin et al. | 310/313 R |
| 5,323,636 | 6/1994 | McGowan et al. | 73/24.06 X |

FOREIGN PATENT DOCUMENTS

| | | | |
|---|---|---|---|
| 282115 | 8/1990 | Germany | 73/24.06 |
| 140838 | 6/1991 | Japan | 73/24.01 |
| 1681229 | 9/1991 | U.S.S.R. | 73/24.01 |
| 1809367 | 4/1993 | U.S.S.R. | 73/23.2 |

OTHER PUBLICATIONS

Grate, J. W. et al. "*Acoustic Wave Microsensors*", Part I, Reprinted form Analytical Chemistry, 65, 940 A–948 A, 1993.

Grate, J. W. et al, "*Acoustic Wave Microsensors*", Part II, Reprinted from Analytical Chemistry, 65, 987 A–996 A, 1993.

Primary Examiner—Hezron E. Williams
Assistant Examiner—Daniel S. Larkin
Attorney, Agent, or Firm—John P. Hohimer; Gregory A. Cone

[57] ABSTRACT

Moisture corrosive gas stream is measured as a function of the difference in resonant frequencies between two acoustic wave (AW) devices, each with a film which accepts at least one of the components of the gas stream. One AW is located in the gas stream while the other is located outside the gas stream but in the same thermal environment. In one embodiment, the film is a hydrophilic material such as $SiO_2$. In another embodiment, the $SiO_2$ is covered with another film which is impermeable to the corrosive gas, such that the AW device in the gas stream measures only the water vapor. In yet another embodiment, the film comprises polyethylene oxide which is hydrophobic and measures only the partial pressure of the corrosive gas. Other embodiments allow for compensation of drift in the system.

24 Claims, 7 Drawing Sheets

FIG. 7

ACOUSTIC WAVE (AW) BASED MOISTURE SENSOR FOR USE WITH CORROSIVE GASES

This invention was made with Government support under Contract No. DE-AC04-76DP00789 awarded by the U.S. Department of Energy. The Government has certain rights in this invention.

BACKGROUND OF THE INVENTION

This invention relates generally to a method and apparatus for detecting trace contaminants in a gas stream and, more specifically, detecting the presence of moisture in a corrosive gas atmosphere using acoustic wave (AW) devices.

At the present time, there is no commercially available solid-state in-line sensor system to detect trace moisture ($H_2O$) in a corrosive atmosphere. Corrosive gases are widely used in a variety of industrial applications, such as semiconductor and pharmaceutical manufacturing. Trace contaminants, like moisture ($H_2O$), in corrosive process gases lead to diminished yields and increased maintenance costs as a result of particle formation and corrosion of equipment. Particle formation is believed to occur as a result of moisture levels as low as 10 ppb in corrosive gases. The obvious solution to the contamination problem is to prevent moisture from being present in the gas stream and to detect moisture upsets during actual gas use. Known ways of preventing $H_2O$ contamination include procedures such as extensive purges, evacuation of plumbing networks, and use of corrosion resistant plumbing networks. However, it is well known in the art that corrosive gases which come in compressed liquid form, such as hydrogen halides like hydrochloric acid (HCl) and hydrogen bromide (HBr), have a time varying $H_2O$ output. As an example, $H_2O$ in the vapor phase from a single tank of compressed liquid HCl can vary from 20 ppm to over 70 ppm as it is consumed. The liquid phase equilibrium constant of the reaction of $H_2O$ in liquid phase HCl can be as much as three orders of magnitude larger than the equilibrium constant for vapor phase HCl. As an example, as the HCl is consumed, the relative concentration of liquid phase $H_2O$ increases due to its lower vapor pressure; the result is an increase in the liquid concentration of $H_2O$ in the HCl which then increases the vapor phase concentration of $H_2O$ in the HCl.

Hence, unacceptable levels of $H_2O$ can be introduced from the HCl gas tank even after careful drying of the distribution system. This demonstrates the need for a low cost, solid-state, in-line sensor system. Although there exist techniques that can detect moisture in a gas stream, such as Karl Fischer titration, infrared spectrometry, and gravimetric procedures using desiccants, there is commercially only one $H_2O$ detection system that will work in a corrosive environment like HCl or HBr. This method of detecting $H_2O$ in a corrosive gas is based on the common chilled mirror dew point/frost point hygrometer. A frost point hygrometer works by chilling the mirror and monitoring its reflectivity as a function of time. By calibrating the apparatus to determine frost formation temperature versus concentration, the $H_2O$ concentration in an unknown sample of the corrosive gas can be determined.

There are several disadvantages to using a frost point hygrometer: first, the moisture concentration measurement requires large volumes of gas to flow across the mirror, at a minimum 1 liter/min. Further, a frost point hygrometer is inherently inaccurate at very low moisture levels (<1 ppm) because of the low rate at which moisture is transported to and condenses on the mirror. Systematic measurement errors occur at low moisture concentrations because the operator tends to cool the mirror past the frost point before the frost is detected, resulting in a measurement which is lower than the actual concentration. Additionally, frost point hygrometers tend to be large, expensive, and not readily adaptable to multi-sensor manufacturing environments. Likewise the output of a frost point hygrometer does not lend itself to integrated signal processing and automated measurements.

The subject invention overcomes these problems by making measurements at a single temperature with an AW device that can detect much smaller amounts of moisture on the surface of the device. This allows the subject invention to provide accurate measurements at very low concentrations of moisture with a minimum gas flow, on the order of 10 ml/min. The present invention, as described, is inherently small, cost effective, and readily adaptable to automation and signal processing.

The detection of trace contaminants such as moisture in inert gases using AW sensor systems has been widely demonstrated in prior art. AW devices in general and Surface Acoustic Wave (SAW) devices more specifically are described in Muller et al. U.S. Pat. No. 4,361,026, Martin et al. U.S. Pat. No. 5,235,235, Frye et al. U.S. Pat. No. 4,947,677, Fletcher U.S. Pat. No. 4,055,072, and Wohltjen U.S. Pat. No. 4,312,228 and are incorporated herein by reference in their entirety.

SUMMARY OF THE INVENTION

This invention relates generally to a method and apparatus for detecting trace contaminants in a gas stream and, more specifically, detecting the presence of moisture in a corrosive gas environment using an acoustic wave device.

It is an object of this invention to provide a sensing means for detecting trace contaminants in a corrosive gas stream using acoustic waves propagated through a given medium and detecting changes in these waves accountable to the trace contaminants.

It is another object of this invention to provide a means for detecting $H_2O$ in a pure corrosive gas stream using an acoustic wave sensor system wherein the sensor devices are coated with a porous hydrophilic dielectric film such as Si or $SiO_2$.

A further object of this invention provides a means for detecting trace contaminants, in particular moisture, in a mixture of a corrosive gas and an inert gas using an acoustic wave (AW) sensor system, wherein one sensor subsystem is coated with a polymer coating, such as Polyethylene Oxide (PEO) or other heterochain-thermoplastics, that will detect the corrosive gas concentration. The other sensor subsystem is coated with a porous hydrophilic dielectric film that will detect the contaminant of interest.

A still further object of this invention provides a means for detecting trace contaminants using an AW sensor system, wherein, the sensor film that detects the corrosive gas concentration could be tuned in thickness, porosity, and composition to make its corrosive gas sensitivity equal to the corrosive gas sensitivity of the moisture sensitive AW device.

Still another feature of the invention is to provide means for detecting moisture in a corrosive gas by using an AW sensor system in conjunction with a moisture trap such that the corrosive gas of interest does not flow across the sensor.

Additional objects, advantages, and novel features of the invention will become apparent to those skilled in the art upon examination of the following description or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and form part of the specification, illustrate an embodiment of the present invention and, together with the description, serve to explain the principles of the invention.

DETAILED DESCRIPTION OF THE INVENTION

Figure 1:
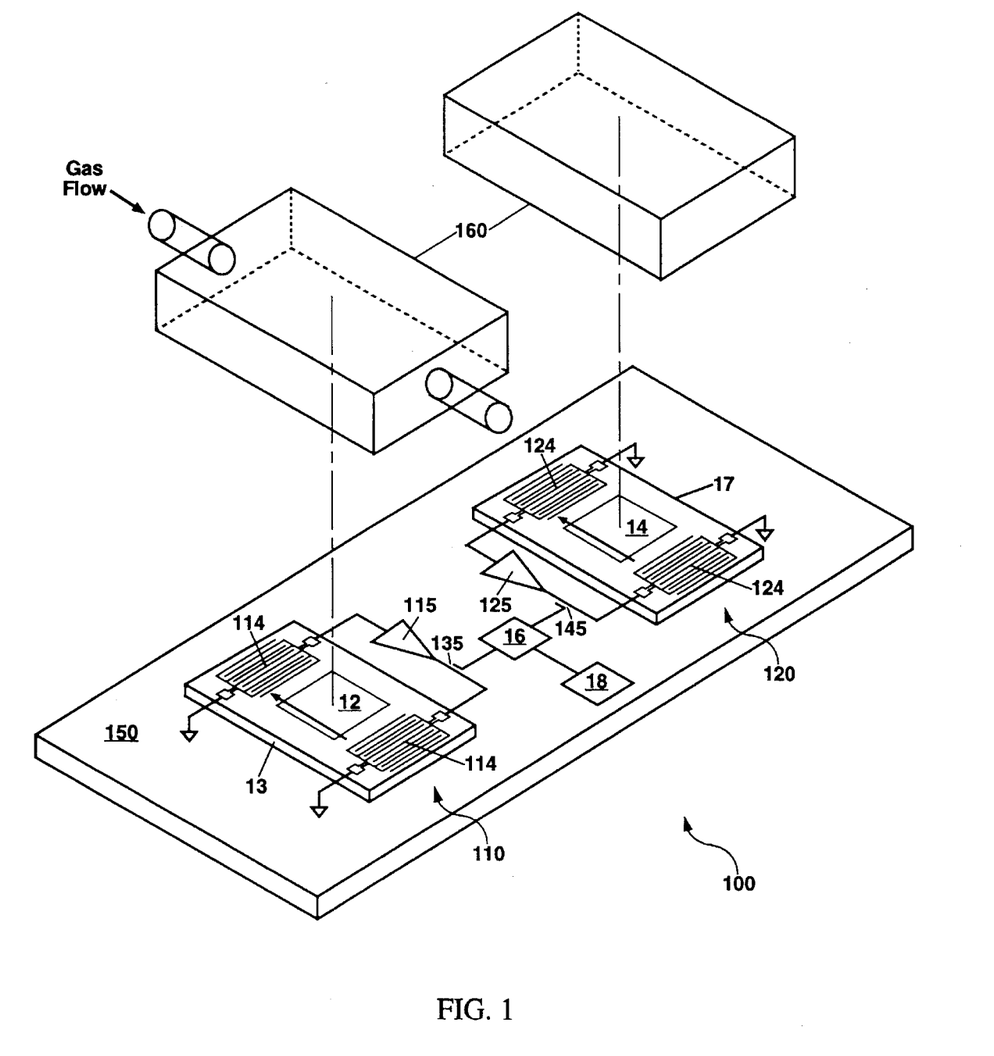
FIG. 1 shows a SAW sensor system with the reference and sensor oscillators depicted.

In the preferred embodiment of the invention disclosed herein, a SAW sensor system used to detect trace moisture in corrosive gases is shown in FIG. 1. The SAW sensor system 100 consists of three elements: a SAW device 110 which will be considered the detector, a SAW device 120 which will be referred to as the reference, and the electronics. In the specific example described herein, substrates 13 and 17, of SAW devices 110 and 120, respectively, are 20 mil ST-cut quartz metallized with 2 nm of chromium and 200 nm of gold or other inert metals. In general, substrates 13 and 17 could be any piezoelectric material. Similarly, a SAW device on a given piezoelectric material can be coated with any conductive material, wherein the maximum thickness of the metal layer is determined by the photolithographic process. The metal layer, as described, was patterned, using photolithographic techniques known to one skilled in the art, to form a pair of interdigital transducers 114 and 124 on each of the substrates 13 and 17, respectively. The area between the interdigital transducers was etched using HF or could be etched using any one of a number of other known etchants to remove surface damage from the substrate. This procedure is necessary to enhance the ability of the device to survive repeated exposures in a corrosive gas environment. A thin porous hydrophilic dielectric material was deposited on the substrates using electron beam techniques to form both the sensing film 12 and the reference film 14. More specifically, the porous hydrophilic dielectric (PHD) film was porous $SiO_2$. For this specific example, the sensing and reference films were a 700 nm layers of porous $SiO_2$. Other porous hydrophilic dielectric films such as porous Si can be deposited using electron beam, sol-gel chemistry, or other similar technology for the sensing and reference film. Both the detector 110 and the reference 120 SAW device are used as feedback elements in oscillator circuits, as shown in U.S. Pat. No. 4,947,677, Frye et al. The combination of a detector SAW device and a reference SAW device that are electrically connected and in thermal communication, wherein both the sensing film and the reference film are a porous hydrophilic dielectric (PHD) material like $SiO_2$ herein will be referred to as a PHD SAW subsystem or $SiO_2$ SAW subsystem. The electronics subsystem consists of RF amplifiers 115 and 125 connected, respectively, across transducer pairs 114 and 124, an RF mixer 16 connected to RF couplers 135 and 145 also connected to the output of each amplifier, and a frequency counter 18 connected to the outputs of mixer 16 to detect the difference frequency between the two oscillator circuits.

To operate the system 100, the reference SAW device 120 is isolated from the atmosphere in question, the corrosive gas, where it is in both thermal and electrical communication with the detector SAW device 110. For this embodiment, each of the SAW devices 110 and 120 is mounted on a thermal mass 150. The thermal mass 150 is typically a conductive metal material like stainless steel or brass. Typically the thermal mass needs to be large enough to accommodate the sensing system. For this embodiment the thermal mass is approximately 2.5 cm×5 cm×1 cm, wherein the SAW devices are approximately 1.0 cm×0.5 cm. The detector SAW device 110 is exposed to the gas atmosphere to be sensed, such as HCl, and detects the trace $H_2O$ in the gas stream by adsorbing $H_2O$ into the porous hydrophilic dielectric film 12 causing a surface disturbance which changes the surface wave velocity. This in turn results in a change in the frequency of the oscillator. Methods used to expose the detector SAW device to the gas atmosphere can be any one of a number of technologies known to one skilled in the art, such as a manifold 160, surrounding the detector SAW device 110 enabling the gas atmosphere to flow directly across the detector SAW device while protecting the reference SAW device as shown in FIG. 1. Any common mode noise such as a change in temperature of the SAW devices 110 and 120 will be observed by both devices and will be nulled out when the two signals are passed through the RF mixer. The output from the RF mixer 16, is filtered such that only the difference frequency is passed and is counted by the frequency counter 18.

Figure 2:
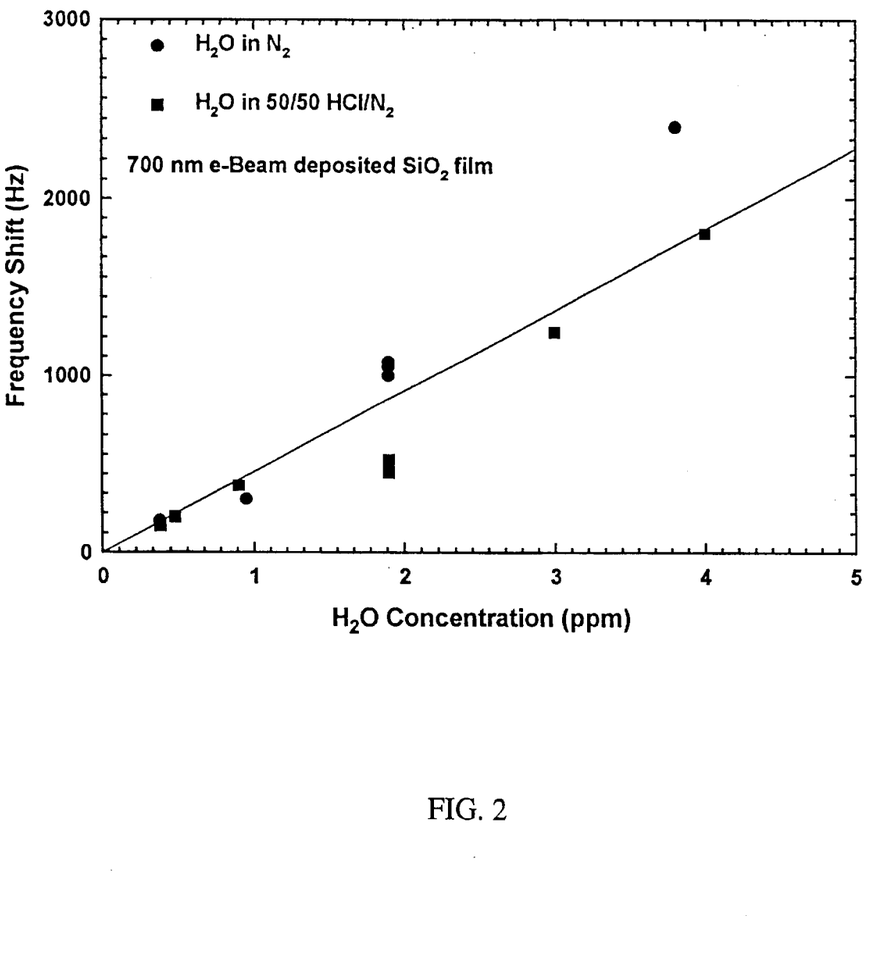
FIG. 2 shows frequency change versus $H_2O$ concentration for the $SiO_2$ sensor system.

The sensor system 100 was tested by exposing the detector SAW device to various concentrations of $H_2O$ in a carrier gas of nitrogen ($N_2$) and dry hydrogen chloride (HCl). The calibration data for a 700 nm electron-beam-deposited film is shown in FIG. 2. SAW devices are inherently sensitive to temperature changes and are therefore typically temperature controlled externally. For the system tested, the temperature of each SAW device was actively controlled at 40° C. with a resolution of less than 0.01° C. FIG. 2 is a plot of the change in frequency versus the concentration of $H_2O$ in ppm for both a carrier gas of dry $N_2$ (filled circles) and a 50/50 mixture of $N_2$ and HCl (triangles). The SAW sensor system responds with a sensitivity of 0.5 Hz/ppb for $H_2O$ in $N_2$ as it does in a mixture of HCl and $N_2$. The sensitivity may be different in other corrosive gases. The minimum detection limit is about 100 ppb of $H_2O$ in either carrier gas for this type of system based on a minimum detectable response of 50 Hz. The robustness of this sensor in a corrosive gas was demonstrated by operating the sensor system in HCl gas for 23 hours over the course of six days with no degradation of the response.

In a similar manner to the sensing system described, a single SAW sensor can be used to detect moisture concentration in a corrosive gas. This single SAW sensor system comprises a single SAW sensor device, like the SAW device 110 in FIG. 1 and an electronics subsystem. For purposes of this example the electronic subsystem could include an amplifier and a frequency detection means capable of detecting a frequency shift attributable to the moisture content, as shown in U.S. Pat. No. 5,117,146 of Martin et al.

Figure 3:
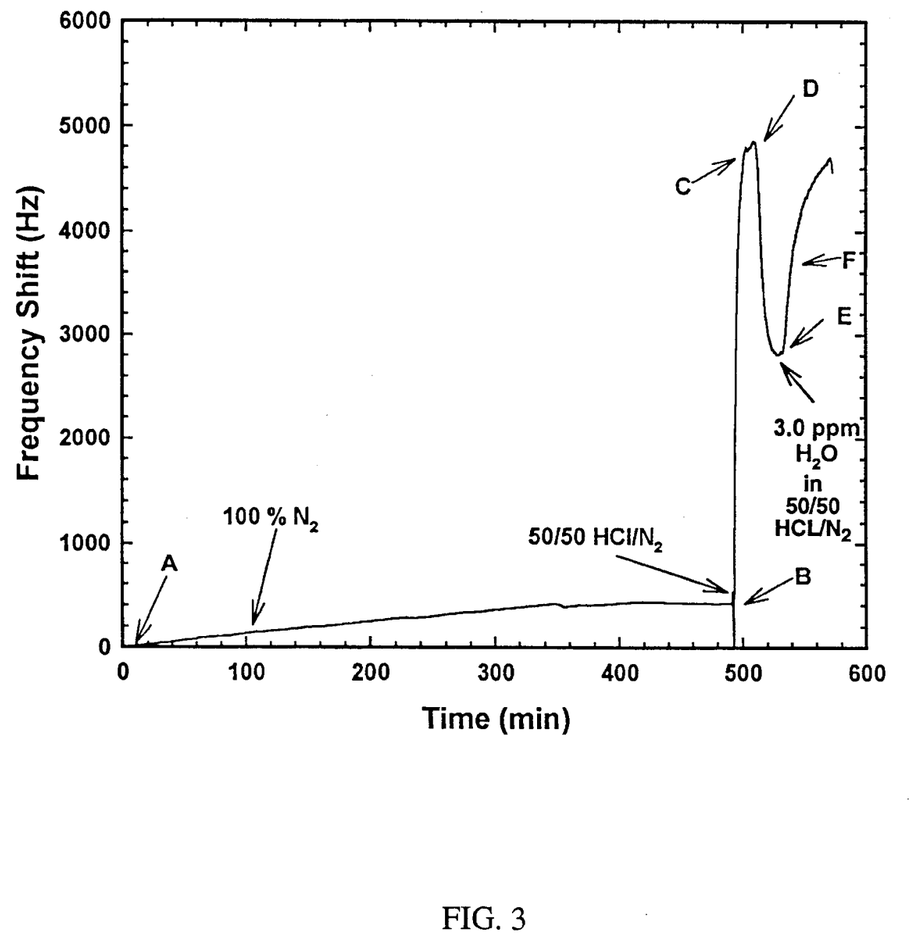
FIG. 3 shows a frequency response for various $N_2$, HCl, and moisture concentrations for a SAW sensor system.

FIG. 3 shows a typical response to a sensor system 100 as shown in FIG. 1, where the sensor film is a 700 nm film of porous $SiO_2$. The response to the sensor system 100 in a pure $N_2$ atmosphere is a very slight increase in the frequency over the first 490 minutes, A to B in FIG. 3. This slight increase in frequency can be attributed to thermal stabilization and drying of the sensor film. When dry HCl is introduced to the test atmosphere a 50/50 mixture is formed and the frequency rapidly increases (B to C) by mass loading of the detector film, until such time as the response stabilizes (C to D). It should be noted that the time between C and D is on the order of 20 minutes. When 3.0 ppm of unwanted $H_2O$ is introduced into the test atmosphere (D), the sensor system frequency response decreases and until such point as it stabilizes (E). The frequency decrease appears to be caused by stiffening of the sensor film. Finally, when the $H_2O$ is removed From the test atmosphere (E to F) the frequency response of the sensor again increases. Since this type of sensor film will respond with a change in frequency after the introduction of HCl as well as for an introduction of $H_2O$, a change in corrosive gas concentration cannot be uniquely distinguished from a change in moisture concentration by this type of sensor.

Figure 5:
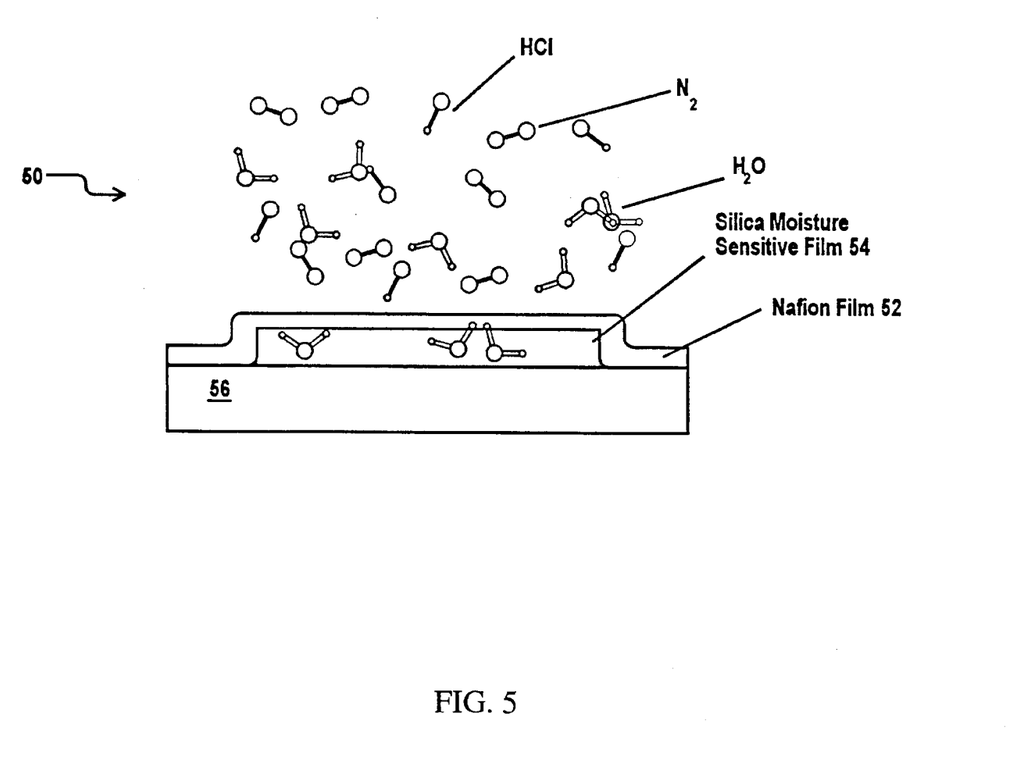
FIG. 5 shows a chemically selective coating over the moisture sensitive coating on a SAW.

An alternative to the SAW device in FIG. 1 is shown FIG. 5. The embodiment shown in FIG. 5, incorporates a second layer of material 54 over the $SiO_2$ sensing film and reference film with a semi-permeable film, such as Nafion™ or other perfluorinated sulfonic acid polymeric material, which prevents the penetration of the corrosive gas into the $SiO_2$ sensing film. This SAW sensor device will only measure the $H_2O$ concentration and not the corrosive gas concentration, because the semi-permeable film 52 has the property of only passing the $H_2O$ to the underlying $SiO_2$ sensing film 54 while blocking the corrosive gas. As before, these films rest on a piezoelectric substrate 56. Thus, the response from this sensor system would only be from the moisture in the gas and not the partial pressure of the corrosive gas. This type of a sensor does not require a corrosive gas compensator circuit because the corrosive gas would not be detected.

Figure 4A:
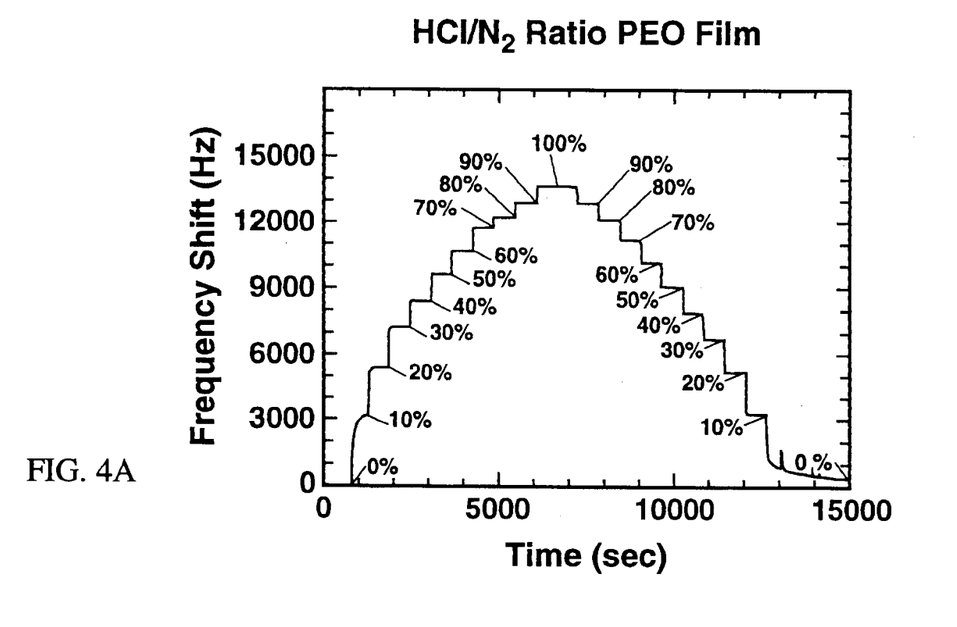
FIG. 4 shows frequency response for the PEO sensor subsystem as a function of time and concentration.
Figure 4B:
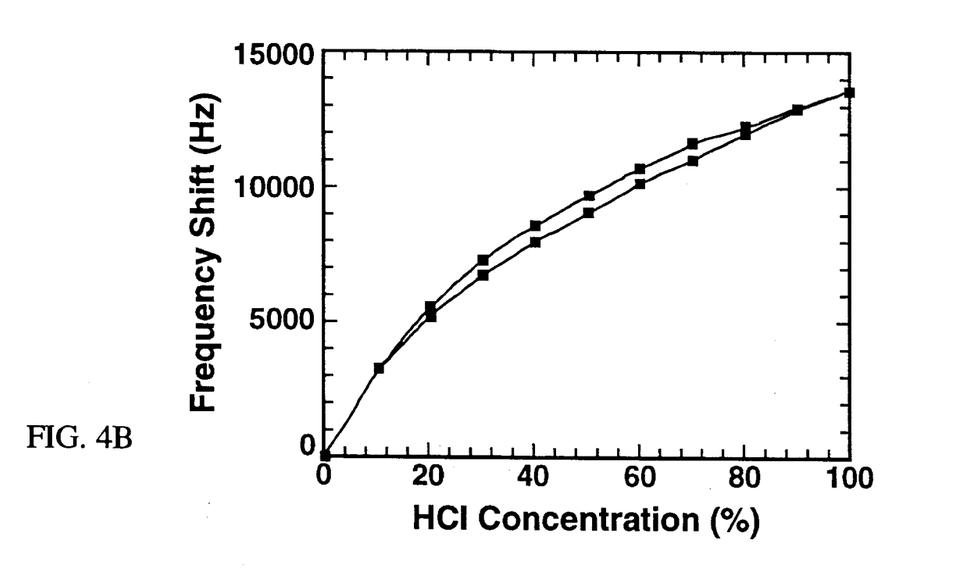
Figure 6:
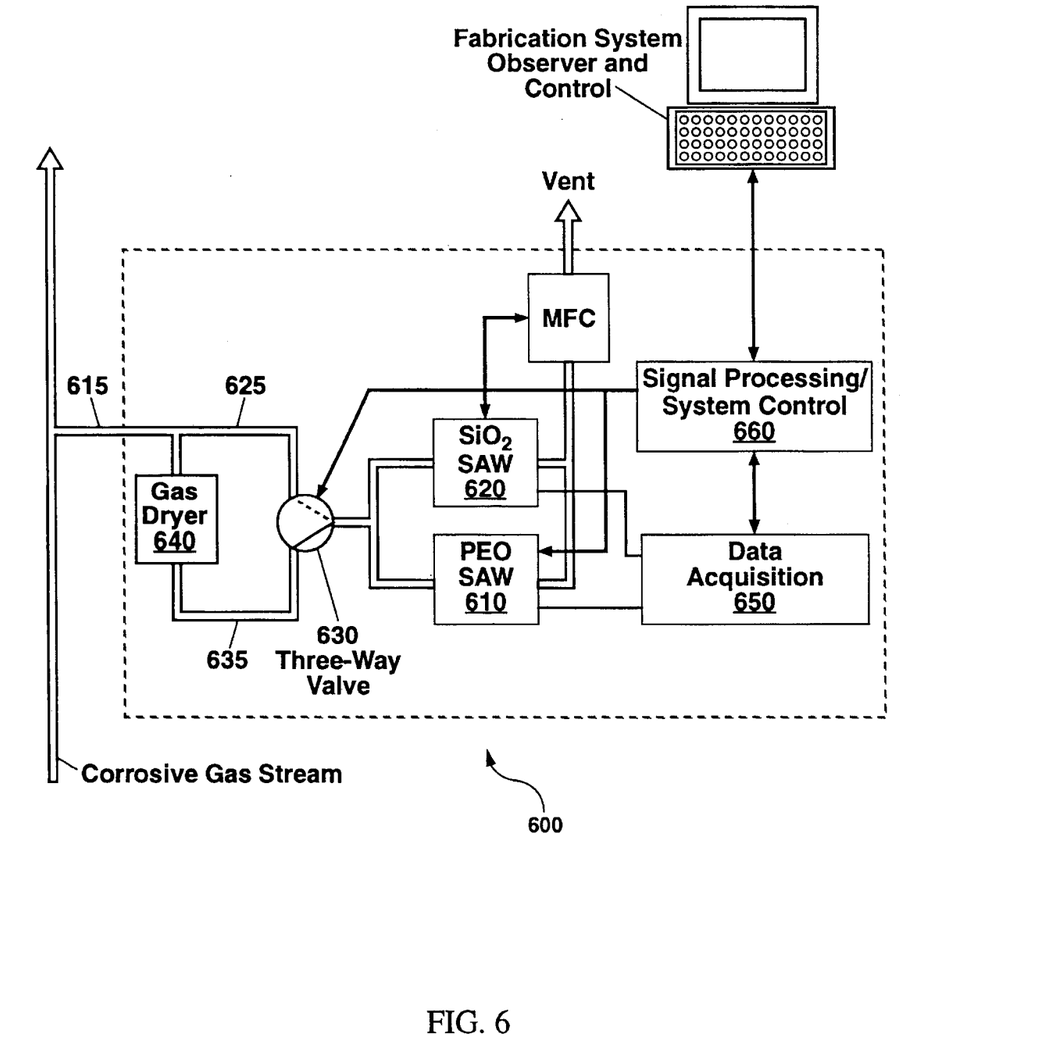
FIG. 6 shows a corrosive gas compensated moisture SAW sensor system.

FIG. 6 is another embodiment of a SAW sensor system for detecting $H_2O$ in a corrosive gas. The sensor system 600 in FIG. 6 incorporates a means for compensating for both the corrosive gas concentration, like HCl or other hydrogen halide, and drift. In order to compensate for the lack of discrimination in gas concentration, it is therefore necessary to employ a sensor that is sensitive to the corrosive gas, in this case HCl, and not the moisture. The SAW sensor system having the capability to detect the corrosive gas and not the moisture is the same as in FIG. 1, with the exception of the $SiO_2$ sensing and reference film 12 and 14 being replaced with polyethylene oxide (PEO) or other heterochain-thermoplastic which is insensitive to the moisture concentration. For this example a 1 weight percent solution of (PEO) was dissolved in benzene and spin cast onto a SAW device. This PEO coated SAW device was capable of providing a compensation signal for the sensor system. The substrate was immersed in acetone and agitated in an ultrasonic cleaner for 15 minutes. The device was then rinsed in methanol and dried with $N_2$. The device was then coated with the PEO solution and spun at 2000 rpm for 30 seconds. Two coats were applied in this manner, and the device was then baked in air for 10 minutes at 150° C. Other polymers having similar characteristics could be used for the sensing and reference film in other corrosive gas atmospheres. Other deposition techniques known to those skilled in the art may be used to form the sensing or reference film. A SAW device having a PEO film will be referred to as hetrochain-thermoplastic (HTP) SAW device as well as a PEO SAW device. An HTP SAW subsystem will refer to a detector SAW and a reference SAW device having a sensing and reference film made from an HTP material electrically connected and in thermal communication. An HTP SAW subsystem was tested for its ability to detect moisture in a corrosive gas via a frequency change. In the case where the HTP SAW subsystem was in an atmosphere of $N_2$ and HCl, no moisture was detected at concentrations below 100 ppm. FIGS. 4a and 4b show the response of the HTP SAW subsystem to various concentrations and mixtures of dry $N_2$ and HCl as the gas mixture is passed over the sensor surface. In a similar fashion, a single PEO SAW device could be used to detect the corrosive gas as described above for the $SiO_2$ system.

In FIG. 6, the PEO SAW sensor subsystem 610 is used to sample the concentration of HCl in the gas stream and to compensate for any change in the partial pressure of the corrosive gas, while an $SiO_2$ SAW sensor subsystem 620 is connected in parallel with the subsystem 610 to detect the trace moisture in the gas. The PEO SAW sensor subsystem 610 comprises two PEO coated SAW devices in the manner of the sensing and reference SAW devices in FIG. 1, while the $SiO_2$ sensor subsystem 620 comprises two $SiO_2$ SAW devices as in FIG. 1. In both the PEO and the $SiO_2$ SAW subsystems, only the detecting SAW devices are exposed to the corrosive gas. In addition, a 3-way electronically controlled valve 630 is employed to alternatively switch the gas from the sample line, 615, to either go directly to the sensing SAWs in subsystems 610 and 620 or to first pass the gas through an HCl dryer 640 which is rated at <100 ppb $H_2O$. By alternating between the gas in line 625 and the dried gas in line 635, a change in moisture concentration would be distinguished from a change in the corrosive gas concentration. The SAW subsystem 620 will respond to the change in moisture level of the corrosive gas while the PEO SAW sensor subsystem 610 will not respond to the change in the moisture level. The PEO SAW sensor subsystem, 610, will only detect a change in HCl concentration, not the moisture concentration. Since the changes in moisture concentration occur rapidly when valve 630 switches, the system can distinguish between moisture effects and long term drift due to other Factors. The advantage of alternating between wet and dry gas is that the sensor is continually re-referenced to the dry gas, and the change in frequency is due to the moisture in the gas.

The data acquisition subsystem 650 collects the frequency outputs from the PEO and $SiO_2$ sensor subsystems and transmits it to the signal processing/system control subsystem 660 which controls the three-way valve 630 and provides data output on gas and moisture concentrations. The implementation of this control system is a matter of routine design to those of ordinary skill in the art.

Figure 7:
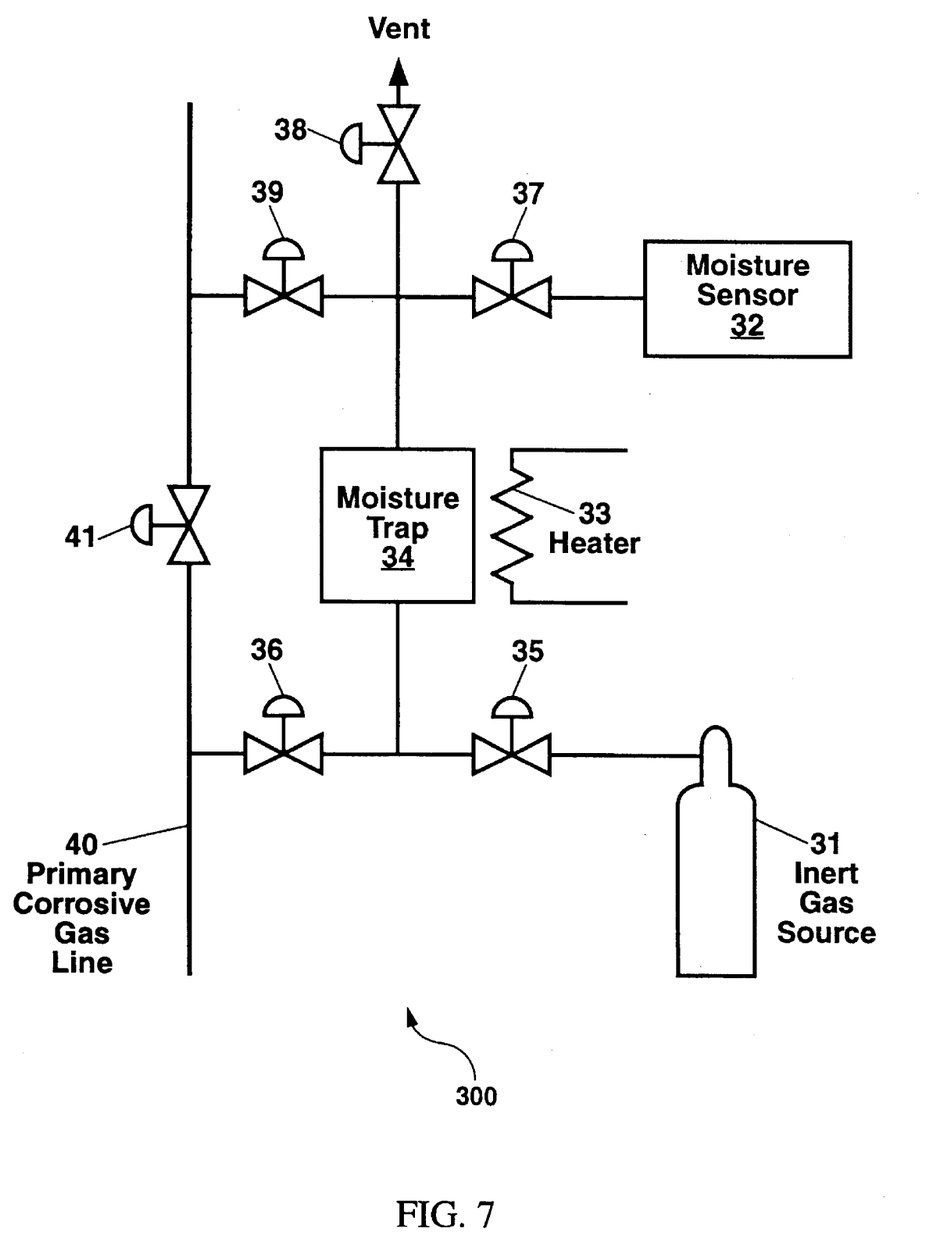
FIG. 7 shows an alternative system to detect moisture in a corrosive gas.

FIG. 7 shows a further embodiment of a moisture sensor system 300. The moisture sensor system 300 works by passing a corrosive gas through a moisture trap 34 and not directly over the sensor. The corrosive gas flow is controlled by closing valves 35, 37, and 38 and opening valves 36 and 39. Additionally, a pressure valve 41 located in the primary gas line 40 causes a pressure differential resulting in a gas flow across the moisture trap, 34. The moisture trap can be either a chemical trap or a physical trap. If the moisture trap is chemical in nature, it should be a chemically adsorbent material like calcium chloride, silica gel, molecular sieve or other like material. If the moisture trap is physical in nature, a refrigeration system is used to cool the trap to a temperature below the frost point of water but above the condensation temperature of the corrosive gas. The gas flow over the moisture trap 34 is continued for a known integration time. Next, valves 36 and 39 are closed and valves 35 and 38 are opened to flush out the residual corrosive gas from the trap and the lines. Valve 38 is then closed and valve 37 is opened. The trap 34 is then heated with a heater 33. The heater 33 can be any known heater technology with the only requirement being that the heater must be capable of maintaining a minimum temperature of 100° C. The gas flow will then be from the inert gas source 31 across the moisture trap and over the moisture sensor 32. The moisture profile from the trap is monitored as a function of time and temperature using the moisture sensor 32. The moisture sensor as described in the sensor system 300, can be any one of a variety of sensors like a SAW sensor similar to the device in FIG. 1. Since the sensor does not get exposed to a corrosive environment, the moisture sensor system 300 provides improved sensitivity and life span. Sensitivity can be increased by trapping the water from a large volume of the corrosive gas and then releasing it into a small volume of inert gas, resulting in an increase in the moisture content of the gas sample being analyzed by the sensor system.

The application of computer-controlled signal processing and system controls could easily be incorporated to any of the above embodiments resulting in automated detection of the moisture concentration and corresponding system response.

The equipment and gas systems discussed above are cited merely to illustrate particular embodiments of this invention. It is contemplated that the use of the invention may involve a variety of components having different sizes, shapes, and materials as long as the principles of the system disclosed herein are followed. For example, although the invention has been disclosed with a SAW device, any acoustic wave device may be used in place of the SAW device with the disclosed films of the invention. Such devices include thickness shear mode resonators (quartz crystal microbalances), acoustic plate mode devices, and flexural plate wave devices. It is intended that the scope of the invention be defined by the claims appended below.

We claim:

1. A sensor system for detecting moisture in a corrosive gas, comprising:
   a) a sensing acoustic wave moisture detector having a sensing film comprising a porous hydrophilic dielectric material, said detector producing a moisture sensing frequency;
   b) a reference acoustic wave moisture detector having a reference film comprising a porous hydrophilic dielectric material, said detector producing a moisture reference frequency;
   c) a sensing acoustic wave corrosive gas detector comprising a corrosive gas sensing film of a heterochain-thermoplastic material, said detector producing a corrosive gas sensing frequency;
   d) a reference acoustic wave corrosive gas detector comprising a corrosive gas reference film of a heterochain-thermoplastic material, said detector producing a corrosive gas reference frequency;
   e) means for controllably extracting the moisture from the corrosive gas to form a dry corrosive gas;
   f) means for alternately directing the flow of the dry corrosive gas and the corrosive gas across the porous hydrophilic dielectric and the heterochain-thermoplastic sensing detectors;
   g) means for generating a first output related to the change in relative frequency between the moisture sensing frequency and the moisture reference frequency;
   h) means for generating a second output related to the change in relative frequency between the corrosive gas sensing frequency and the corrosive gas reference frequency; and
   i) means for combining the first and second output, thereby determining the moisture content in the corrosive gas.

2. The sensor system of claim 1, wherein the porous hydrophilic dielectric material is selected from the group consisting of silicon and silicon dioxide.

3. The sensor system of claim 1, wherein the heterochain-thermoplastic material is polyethylene oxide.

4. The sensor system of claim 1, wherein the corrosive gas comprises a hydrogen halide.

5. The sensor system of claim 1, wherein said sensor system can detect 100 parts-per-billion of moisture in said corrosive gas.

6. The sensor system of claim 1, wherein said means for controllably extracting the moisture from the corrosive gas produces dry corrosive gas having less than 100 parts-per-billion of moisture.

7. The sensor system of claim 1, wherein said acoustic wave detectors are based on surface acoustic wave devices.

8. The sensor system of claim 1, further comprising:
   a) the use of said means for controllably extracting the moisture from the corrosive gas to trap said moisture during a period of exposure to said corrosive gas;
   b) extension of said means for alternately directing the flow of the dry corrosive gas and the corrosive gas across the porous hydrophilic dielectric and heterochain-thermoplastic sensing detectors to the diversion of corrosive gas and of dry corrosive gas away from said means for controllably extracting the moisture from the corrosive gas and from said detectors;
   c) means for flushing residual corrosive gas from the means for controllably extracting the moisture from the corrosive gas;
   d) means for heating the means for controllably extracting the moisture from the corrosive gas so as to vaporize the moisture contained therein;
   e) means for sensing the presence of said vaporized moisture and forming a sensing signal therefrom; and
   f) means for combining said period of exposure and said sensing signal into an output signal reflecting the concentration of moisture in the corrosive gas.

9. The sensor system of claim 8, wherein the means for sensing the presence of said vaporized moisture comprises a surface acoustic wave device.

10. The sensor system of claim 8, wherein said sensor system has a minimum detection level of 100 parts-per-billion moisture in the corrosive gas.

11. The sensor system of claim 8, wherein said means for controllably extracting the moisture from the corrosive gas comprises an adsorbent material selected from the group consisting of calcium chloride, silica gel, and molecular sieve.

12. The sensor system of claim 8, wherein said means for controllably extracting the moisture from the corrosive gas comprises a cold trap.

13. The sensor system of claim 12, wherein said cold trap further comprises an inert packing material.

14. The sensor system of claim 4, wherein the hydrogen halide corrosive gas is selected from the group consisting of hydrochloric acid (HCl) and hydrogen bromide (HBr).

15. The sensor system of claim 4 wherein each detector comprises an acoustic wave device selected from the group consisting of surface acoustic wave devices, thickness shear mode resonator devices, acoustic plate mode devices, and flexural plate wave devices.

16. A sensor system for detecting moisture in a corrosive gas, comprising:
   a) an acoustic wave moisture sensor comprising a moisture-sensing film of a porous hydrophilic dielectric material and providing a first frequency output responsive, at least in part, to the moisture in the corrosive gas;
   b) an acoustic wave corrosive gas sensor comprising a corrosive gas sensing film of a heterochain-thermoplastic material and providing a second frequency output responsive to a concentration of the corrosive gas; and
   c) means for comparing the first and second frequency outputs for determining the moisture content in the corrosive gas.

17. The sensor system of claim 16, wherein each sensor comprises a pair of acoustic wave devices formed on a common substrate, with one of the devices in each pair being isolated from exposure to the corrosive gas.

18. The sensor system of claim 16, wherein the first frequency output comprises a difference in frequencies provided by a sensing acoustic wave device and a reference acoustic wave device of the moisture sensor, and the second frequency output comprises a difference in frequencies provided by a sensing acoustic wave device and a reference acoustic wave device of the corrosive gas sensor.

19. The sensor system of claim 16, wherein the means for combining the first and second frequency outputs includes a data acquisition subsystem.

20. The sensor system of claim 16 wherein each sensor comprises at least one acoustic wave device selected from the group consisting of surface acoustic wave devices, thickness shear mode resonator devices, acoustic plate mode devices, and flexural plate wave devices.

21. The sensor system of claim 16, wherein the porous hydrophilic dielectric material is a deposited material selected from the group consisting of silicon and silicon dioxide.

22. The sensor system of claim 16, wherein the heterochain-thermoplastic material comprises polyethylene oxide.

23. The sensor system of claim 16, wherein the corrosive gas comprises a hydrogen halide.

24. The sensor system of claim 23, wherein the hydrogen halide corrosive gas is selected from the group consisting of hydrochloric acid (HCl) and hydrogen bromide (HBr).

* * * * *